(12) United States Patent
Radmand

(10) Patent No.: US 11,191,663 B2
(45) Date of Patent: *Dec. 7, 2021

(54) ORAL APPLIANCE AND KIT FOR TREATMENT OF SLEEP APNEA

(71) Applicant: Achaemenid, LLC, Stratford, CT (US)

(72) Inventor: Reza Radmand, Boston, MA (US)

(73) Assignee: Achaemenid, LLC

( * ) Notice: Subject to any disclaimer, the term of this patent is extended or adjusted under 35 U.S.C. 154(b) by 298 days.

This patent is subject to a terminal disclaimer.

(21) Appl. No.: 16/593,046

(22) Filed: Oct. 4, 2019

(65) Prior Publication Data

US 2020/0038231 A1 Feb. 6, 2020

Related U.S. Application Data

(63) Continuation of application No. 15/479,737, filed on Apr. 5, 2017, now Pat. No. 10,470,921.

(Continued)

(51) Int. Cl.
*A61F 5/56* (2006.01)
*A61N 1/36* (2006.01)
(Continued)

(52) U.S. Cl.
CPC ............ *A61F 5/566* (2013.01); *A61B 5/0816* (2013.01); *A61B 5/14552* (2013.01);
(Continued)

(58) Field of Classification Search
CPC ... A61F 5/566; A61N 1/0548; A61N 1/36139; A61N 1/3611; A61N 1/36146;
(Continued)

(56) References Cited

U.S. PATENT DOCUMENTS 3,599,629 A 8/1971 Gordy
4,629,424 A 12/1986 Lauks et al.
(Continued)

FOREIGN PATENT DOCUMENTS

AU 2002100414 B4 11/2002
CN 1823691 A 8/2006
(Continued)

OTHER PUBLICATIONS

International Searching Authority, International Search Report and Written Opinion of PCT App. No. PCT/US20/16597, dated Apr. 27, 2020, 16 pgs.

(Continued)

*Primary Examiner* — Tarla R Patel
(74) *Attorney, Agent, or Firm* — Moyles IP, LLC

(57) ABSTRACT

An oral appliance for the treatment of obstructive sleep apnea includes a mouthpiece configured for being received in an oral cavity of a user. The mouthpiece may include a pulse oximeter, a pressure sensor, an airflow sensor, an actigraphy sensor, a noise detector, and at least one stimulator for providing stimulation to a user's tongue in the event of decreased oxygen saturation levels, increased pressure applied to occlusal surfaces of the user's dentition, decreased actual airflow levels and/or increased noise levels. A microprocessor receives data from the oxygen sensor, pressure sensor, airflow sensor, actigraphy sensor and noise detector, and activates the at least one stimulator.

20 Claims, 5 Drawing Sheets

Related U.S. Application Data

(60) Provisional application No. 62/319,443, filed on Apr. 7, 2016.

(51) Int. Cl.
*A61B 5/1455* (2006.01)
*A61B 5/08* (2006.01)
*A61B 5/00* (2006.01)
*A61N 1/05* (2006.01)
*A61N 1/08* (2006.01)

(52) U.S. Cl.
CPC .......... *A61B 5/4806* (2013.01); *A61N 1/0548* (2013.01); *A61N 1/3611* (2013.01); *A61N 1/36139* (2013.01); *A61N 1/08* (2013.01); *A61N 1/3601* (2013.01); *A61N 1/36078* (2013.01); *A61N 1/36146* (2013.01)

(58) Field of Classification Search
CPC .... A61N 1/36078; A61N 1/3601; A61N 1/08; A61B 5/0816; A61B 5/14552; A61B 5/4806
See application file for complete search history.

(56) References Cited

U.S. PATENT DOCUMENTS

| | | | |
|---|---|---|---|
| 4,777,954 | A | 10/1988 | Keusch et al. |
| 5,190,053 | A | 3/1993 | Meer |
| 5,212,476 | A | 5/1993 | Maloney |
| 5,284,161 | A | 2/1994 | Karell |
| 5,490,520 | A | 2/1996 | Schaefer et al. |
| 5,765,563 | A | 6/1998 | Vander Schaaf |
| 5,792,067 | A | 8/1998 | Karell |
| 6,212,435 | B1 | 4/2001 | Lattner et al. |
| 6,418,933 | B1 | 7/2002 | Strong |
| 6,536,439 | B1 | 3/2003 | Palmisano |
| 6,598,006 | B1 | 7/2003 | Honda et al. |
| 6,604,527 | B1 | 8/2003 | Palmisano |
| 7,216,648 | B2 | 5/2007 | Nelson et al. |
| 7,690,378 | B1 | 4/2010 | Turcott |
| 7,711,438 | B2 | 5/2010 | Lattner et al. |
| 7,885,708 | B2 | 2/2011 | Shanks et al. |
| 8,751,005 | B2 | 6/2014 | Meadows et al. |
| D718,448 | S | 11/2014 | Bedford et al. |
| D718,449 | S | 11/2014 | Bedford et al. |
| 10,195,426 | B2 | 2/2019 | Kent et al. |
| 10,195,427 | B2 | 2/2019 | Kent et al. |
| 10,376,202 | B2 | 8/2019 | Shah et al. |
| 10,376,210 | B2 | 8/2019 | Paris et al. |
| 10,420,672 | B2 | 9/2019 | Hermanson et al. |
| 10,470,921 | B2 * | 11/2019 | Radmand .............. A61B 5/0816 |
| 11,000,405 | B2 * | 5/2021 | Radmand .............. A61N 1/36031 |
| 2005/0113654 | A1 | 5/2005 | Weber et al. |
| 2007/0173893 | A1 | 7/2007 | Pitts |
| 2008/0233541 | A1 | 9/2008 | Vreese et al. |
| 2009/0082839 | A1 | 3/2009 | Lindquist et al. |
| 2009/0210032 | A1 | 8/2009 | Beiski et al. |
| 2009/0281433 | A1 | 11/2009 | Saadat et al. |
| 2010/0204614 | A1 | 8/2010 | Lindquist et al. |
| 2010/0204747 | A1 | 8/2010 | Lindquist et al. |
| 2013/0109932 | A1 | 5/2013 | Saadat et al. |
| 2013/0211270 | A1 | 8/2013 | St. Laurent et al. |
| 2013/0253286 | A1 | 9/2013 | Fridman |
| 2014/0114165 | A1 | 4/2014 | Walker et al. |
| 2014/0135868 | A1 | 5/2014 | Bashyam |
| 2014/0323839 | A1 | 10/2014 | McCreery |
| 2015/0190630 | A1 | 7/2015 | Kent et al. |
| 2015/0217115 | A1 | 8/2015 | Avitall |
| 2016/0199215 | A1 | 7/2016 | Kopelman |
| 2017/0196727 | A1 | 7/2017 | Giridharagopalan |
| 2018/0000563 | A1 | 1/2018 | Shanjani et al. |
| 2018/0116863 | A1 | 5/2018 | Shah et al. |
| 2018/0177570 | A1 | 6/2018 | Alauddin et al. |
| 2019/0029587 | A1 | 1/2019 | Walker et al. |
| 2019/0057700 | A1 | 2/2019 | Kent et al. |
| 2019/0133730 | A1 | 5/2019 | Adams et al. |
| 2020/0060611 | A1 * | 2/2020 | Radmand .............. A61B 5/1116 |

FOREIGN PATENT DOCUMENTS

| | | | |
|---|---|---|---|
| CN | 104921833 | A | 9/2015 |
| EP | 3318216 | B1 | 2/2020 |
| JP | 2018000930 | A | 1/2018 |
| KR | 101645870 | B1 | 8/2016 |
| KR | 20160095425 | A | 8/2016 |
| WO | 2008048649 | A2 | 4/2008 |
| WO | 2012027648 | A2 | 3/2012 |
| WO | 2012027648 | A3 | 8/2012 |
| WO | 2014107446 | A1 | 7/2014 |
| WO | 2016087813 | A1 | 6/2016 |

OTHER PUBLICATIONS

United States Patent and Trademark Office, Office Action of U.S. Appl. No. 16/781,417, dated Apr. 16, 2020, 14 pgs.

Castaneda, et al.; A review on wearable photoplethysmography sensors and their potential future application in health care; International Journal of Biosensors & Bioelectronics; dated Mar. 20, 2019; 19 pages.

European Respiratory Journal, Severity of obstructive sleep apnoea/hypopnoea syndrome and subsequent waking EEG spectral power, vol. 32, No. 3, Jun. 5, 2012, 6 pgs., https://erj.ersjournals.com/content/32/3/705.short.

International Searching Authority, Written Opinion of PCT Publication No. WO2014107466, dated Mar. 19, 2014, 4 pages.

National Institute of Health Public Access Author Manuscript, EEG Recording and Analysis for Sleep Research, Oct. 2009, 21 pgs., https://www.ncbi.nlm.nih.gov/pmc/articles/PMC2824445/.

United States Patent and Trademark Office; Final Office Action for U.S. Appl. No. 16/781,417 dated Nov. 17, 2020; 17 pages.

Very Well Health, Electronic Tongue Device for Sleep Apnea, dated Apr. 29, 2019, 4 pgs., https://www.verywellhealth.com/hypoglossal-nerve-stimulator-for-treating-sleep-apnea-3015195.

Lizette Borreli, Sleep Apnea May Increase Pneumonia Risk; CPAP May Increase Pulmonary Aspiration, Bacteria, Medical Daily, Mar. 3, 2014, 10 pages, http://www.medicaldaily.com/.

Tekscan, Inc., Measure Force with FlexiForce Force Sensors, 8 pages, Apr. 12, 2015, https://www.tekscan.com/product-group/embedded-sensing/force-sensors.

Arie Oliven, Treating Obstructive Sleep Apnea With Hypoglossal Nerve Stimulation, Medscape, Nov. 8, 2011, 9 pages, http://search.medscape.com/search/?q=Arie%20Oliven.

Norman Wolkove, et al., Long-term compliance with continuous positive airway pressure in patients with obstructive sleep apnea, Oct. 2008, 8 pages, www.ncbi.nlm.nih.gov/.

Wikipedia, Pulse Oximetry, Wikipedia, Oct. 1, 2004, 9 pages, https://en.wikipedia.org/wiki/Pulse_oximetry.

Nyxoah, Enjoy the comfort of Restful Nights, Aug. 27, 2016, 3 pages, http://www.nyxoah.com/patients/what-is-osa.

Nyxoah, Sleep Apnea—Nyxoah, 2015, 5 pages, http://www.nyxoah.com/sleep-apnea.

Researchgate, Sublingual electrical stimulation of the tongue during wakefulness and sleep, Sep. 2001, 1 page, https://www.researchgate.net/publication/11839659.

True Wearables, Oxxiom—Expand Your Limits Control What You Can Measure Aim Higher, 2015, 5 pgs., https://www.truewearables.com/.

* cited by examiner

ORAL APPLIANCE AND KIT FOR TREATMENT OF SLEEP APNEA

CROSS-REFERENCE TO RELATED APPLICATIONS

This application is a continuation of U.S. application Ser. No. 15/479,737 filed Apr. 5, 2017, which claims the benefit of U.S. Provisional Application No. 62/319,443 filed Apr. 7, 2016, each of which is incorporated herein by reference in its entirety.

FIELD

A device and a method for providing treatment of sleep disorders, such as obstructive sleep apnea, in a user is generally described.

BACKGROUND

Sleep apnea is a common medical condition during which a person experiences one or more pauses in breathing and/or shallow breaths during sleep. While there are several types of sleep apnea, the most common type is obstructive sleep apnea. In this medical condition, one or more of the person's throat muscles relax during sleep causing surrounding tissues in the posterior portions of the mouth, nose and throat to collapse, thereby creating a pharyngeal obstruction that can block the upper airway. Persons suffering from obstructive sleep apnea have inadequate oxygen exchange during sleep, which can lead to daytime fatigue, lack of concentration and mood changes. Left untreated, obstructive sleep apnea can have a significant impact on a person's health, often leading to cardiovascular, stroke and metabolic disorders.

Known methods for treatment of obstructive sleep apnea include both surgical and nonsurgical devices. A popular surgical procedure is uvulopalatopharyngoplasty, which may be performed for patients who have anatomical abnormalities that cause their obstructive sleep apnea and/or make them less likely to tolerate nonsurgical devices. Uvulopalatopharyngoplasty may be a complicated surgery, during which a portion of the soft palate is removed in an effort to prevent closure of the airway by excess tissue during sleep. A disadvantage of this procedure, however, is that the operation is often expensive and may damage throat muscles necessary for swallowing and/or cause other undesirable disorders, such as, nasal regurgitation and numbness of the lower front teeth.

To reduce this risk, various nonsurgical approaches have been employed. One such nonsurgical approach includes using standardized oral appliances to incrementally advance and/or protrude the mandible (lower jaw) relative to the maxilla (upper jaw). These standardized oral appliances, commonly referred to as a mandibular advancement device, ("MAD"), typically include upper and lower dental trays, whereby the lower dental tray is designed to advance the mandible, and hence, move the tongue forward to increase the space in the posterior part of the throat and the oropharynx, which in turn may serve to increase the flow of air during sleep. The distance (degree of advancement) required to protrude and/or reposition the mandible may be, at least in part, dependent on the severity of the individual's obstructive sleep apnea, as well as psychological variables among the users. A disadvantage of using these standard oral appliances is that they may not sufficiently provide for and/or address individualized anatomical variances, such as difference in dental arches, dentition alignment and/or jaw flexibility. Another disadvantage is that in instances where the degree of advancement is excessive, the appliance may lead to long-term temporomandibular joint ("TMJ") disorders, muscular aggravation, dentition discomfort and/or myofascial disorders. As a result, use of these standard appliances has an approximate compliance rate of 75% over a 2-year period. For a detailed study of compliance with use of MAD, see *Non-CPAP therapies in obstructive sleep apnoea: mandibular advancement device therapy*, see Eur Respir J 2012; 39: 1241-1247, which is incorporated by reference in its entirety. Thus, such oral appliances may not treat obstructive sleep apnea in a manner that prevents and/or limits impacts on a person's health.

FIG. 1 depicts a system 1 including an intraoral stimulator device 2 used for providing treatment of a sleep disorder. The intraoral stimulator device 2 is powered by a rechargeable battery and includes a housing 4 of a hollow dental retainer wire-frame or mouth-guard (in the case of a bilateral configuration) or a molar teeth clip (in the case of unilateral configuration) for positioning on the lower teeth. The housing 4 includes a single pair or two pairs of bilateral electrodes 5a, 5b for positioning ventral-laterally and sublingually at the posterior to middle section under the tongue for recruiting a large section of the genioglossus muscle and base-of-tongue for stimulation to regain muscle tone during sleep. The system 1 includes an external inductive recharger sub-system 6, configured to receive electrical power from a wall outlet 7 and use the electrical power to recharge a rechargeable battery (not shown) provided in the intraoral stimulator device 2 by transferring power through electromagnetic induction. The oral appliance 1 further includes a non-rechargeable battery operated hand-held appliance 3 that communicates instructions to the intraoral stimulator device 2. The non-rechargeable battery operated hand-held appliance 3 is used by the patient's sleep medicine physician to program the stimulation and to set system parameters in the intraoral stimulator device 2. The stimulation can be pre-programmed or can occur as a result of change in the user's breathing pattern, as tested by accelerometer, temperature, piezoelectric film and EMG. Alternatively, the stimulation therapy may be programmed and setup up by a physician so that the therapy begins as soon as the device is turned On and ceases when the device turns Off, without regard to changes in the user's breathing pattern. An issue with continuous stimulation is that over stimulation can lead to nerve and/or muscle fatigue/damage. Moreover, while a physician can set and/or send instructions to the intraoral stimulator, the physician cannot store and or assess the breathing and/or snoring pattern of a patient in a way that allows the physician to modify treatment as may be necessary. The lack of specialized treatment measures in individual patients with unique medical needs can be problematic, particularly because they fail to store patient behavior and/or medical data that can assist medical providers in the design and/or improvement of specialized treatment measures for individual patients. Thus, such intraoral stimulator devices may fail to treat obstructive sleep apnea in a manner that prevents and/or limits impacts on a person's health.

Other methods of treating obstructive sleep apnea include the administration of positive air pressure via a continuous positive airway pressure ("CPAP") machine. The CPAP machine is often assembled for use in combination with various face or nasal masks and may provide continuously pressurized and/or forced air during the person's sleep. A disadvantage of this assembly is that it may cause nasal and/or oral mucosal dryness due to the continuously forced air and may also cause claustrophobia due to the presence of a mask on the patient's face. As a result, use of these assemblies has an approximate compliance rate of 50% over a 5-year period. For a detailed study of compliance with use of CPAP machines, see *Long-term compliance with continuous positive airway pressure in patients with obstructive sleep apnea*, Can Respir J. 2008 October; 15(7): 365-369, which is incorporated by reference in its entirety. Another disadvantage is that standard masks are not properly adapted for a customized fit for persons with unique and/or variable facial anatomies that may be natural or created by loss of muscle tone secondary to facial paralysis and/or stroke. Ill-fitting masks may lead to leakage of air and/or inadequate air intake. In addition, the masks used with CPAP machines have been found to be a breeding ground for bacteria and fungi. Despite routine washing and cleaning measures, the bacteria and fungi on these masks can grow exponentially, and lead to infections, such as pneumonia, in the airways of persons who use them. Moreover, such assemblies may not sufficiently treat obstructive sleep apnea and may fail to promote patient compliance with the treatment method.

The aforementioned treatment techniques may not provide sufficient treatment of obstructive sleep apnea, may cause and/or promote other negative health situations for the user and may not foster compliance with treatment methods.

In view of the disadvantages associated with currently available methods and devices for treating obstructive sleep apnea, there is a need for a device and method that treats obstructive sleep apnea while storing patient behavior and/or medical data relating to a user's breathing pattern, snoring pattern and/or clenching/grinding behaviors, that can assist medical providers in the design, improvement and/or modification of specialized treatment measures for individual patients. Further, there is a need for a device and method that treats obstructive sleep apnea in a single removable oral appliance and prevents and/or limits long-term TMJ disorders, muscular aggravation and/or myofascial disorders that may occur with continued use of currently available appliances.

BRIEF DESCRIPTION

According to an aspect, the present embodiments may be associated with an oral appliance for the treatment of sleep disorders, such as obstructive sleep apnea, and reducing clenching and/or grinding of teeth in a user. The oral appliance may include a mouthpiece configured to receive a dentition of a user. The mouthpiece may include various electronic components including an oxygen sensor and at least one stimulator for providing stimulation to a user's tongue in the event of decreased oxygen saturation levels. According to an aspect, the mouthpiece includes one or more pressure sensors, an airflow sensor, a noise detector and an actigraphy sensor. The mouthpiece may further include a microprocessor that receives data from the oxygen sensor, the pressure sensor, the airflow sensor, the noise detector and the actigraphy sensor, and activates the at least one stimulator in the event of decreased oxygen saturation levels, increased pressure applied to occlusal surfaces of the user's dentition, decreased airflow and increased noise levels.

BRIEF DESCRIPTION OF THE FIGURES

A more particular description will be rendered by reference to specific embodiments thereof that are illustrated in the appended drawings. Understanding that these drawings depict only typical embodiments thereof and are not therefore to be considered to be limiting of its scope, exemplary embodiments will be described and explained with additional specificity and detail through the use of the accompanying drawings in which.

and

Figure 6:
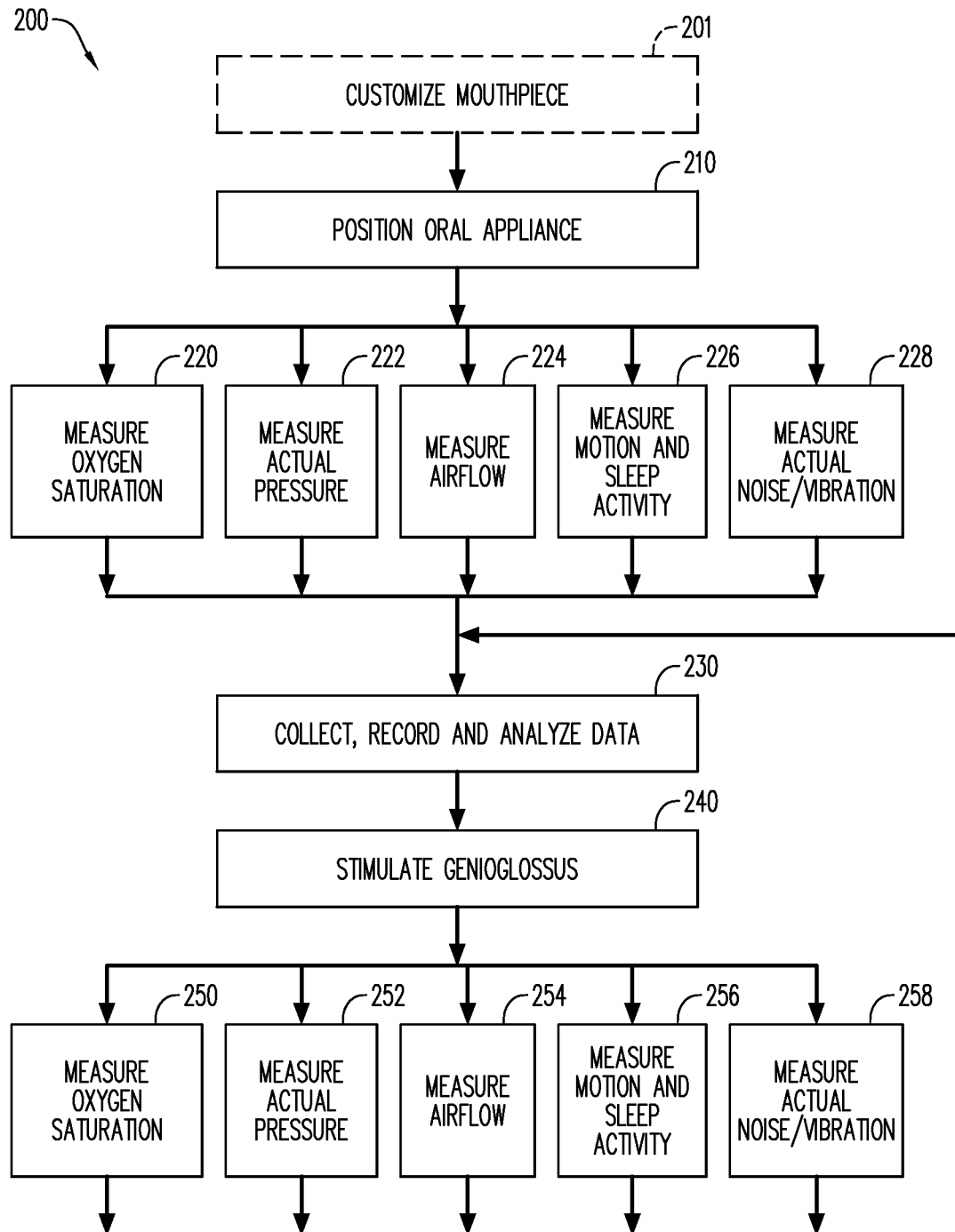

FIG. 6 is a schematic of a method for providing electrical genioglossus stimulation, according to an embodiment.

Various features, aspects, and advantages of the embodiments will become more apparent from the following detailed description, along with the accompanying figures in which like numerals represent like components throughout the figures and text. The various described features are not necessarily drawn to scale, but are drawn to emphasize specific features relevant to some embodiments.

DETAILED DESCRIPTION

Reference will now be made in detail to various embodiments. Each example is provided by way of explanation, and is not meant as a limitation and does not constitute a definition of all possible embodiments.

Embodiments of the disclosure related generally to devices and methods for treating obstructive sleep apnea, as well as a device for providing electrical stimulation to a user's tongue to inhibit and/or limit snoring that may be caused by obstructive sleep apnea. Such devices provide particular utility in providing electrical stimulation to the user's tongue in such a manner that the stimulation does not awaken the user during sleep. The oral appliance contemplated includes a mouthpiece that is configured to receive at least temporary, permanent and/or artificial lower dentition of the user. The mouthpiece may include various electronic components including one or more of the following: an oxygen sensor, a pressure sensor, an airflow sensor, a noise detector, an actigraphy sensor, a stimulator, data recorder, battery and a microprocessor. The mouthpiece may include customizable materials that provide a comfortable fit for a user while retrieving data related to the user's oxygen saturation levels, clenching and/or grinding of dentition surfaces, actual airflow levels and noise levels associated with snoring, analyzing the data, and preparing a set of instructions to the stimulator.

According to an aspect, the mouthpiece is customized to be receivably positioned and/or secured on the mandible of the user. According to an aspect, the mouthpiece is customized to receive the lower dentition of the user. In any event the mouthpiece may be customized such that it provides a comfortable fit that enhances the user's comfort and reinforces the user's likelihood of repeated wear of the mouthpiece, i.e., the user's compliance rate.

For purposes of illustrating features of the embodiments, a simple example will now be introduced and referenced throughout the disclosure. Those skilled in the art will recognize that this example is illustrative and not limiting and is provided purely for explanatory purposes.

Figure 1:
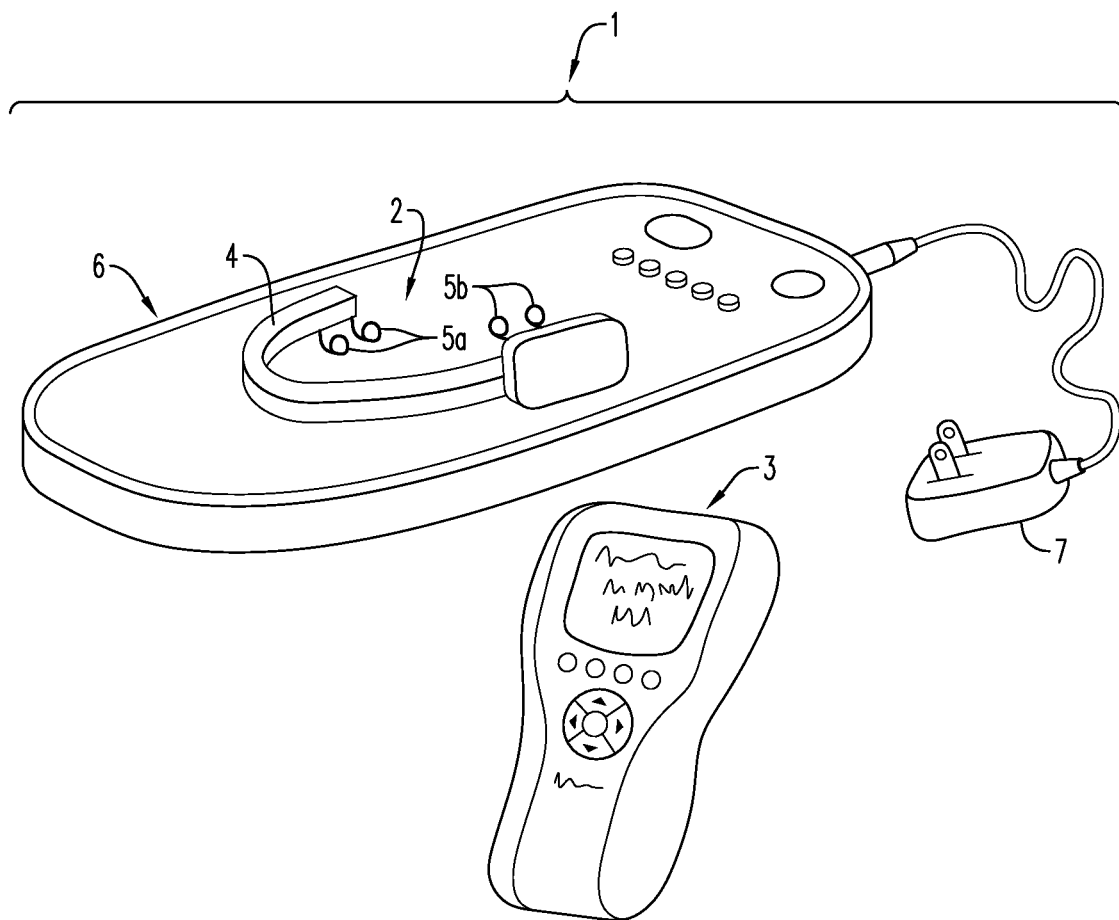
FIG. 1 is a perspective view of a prior art oral device.
Figure 2:
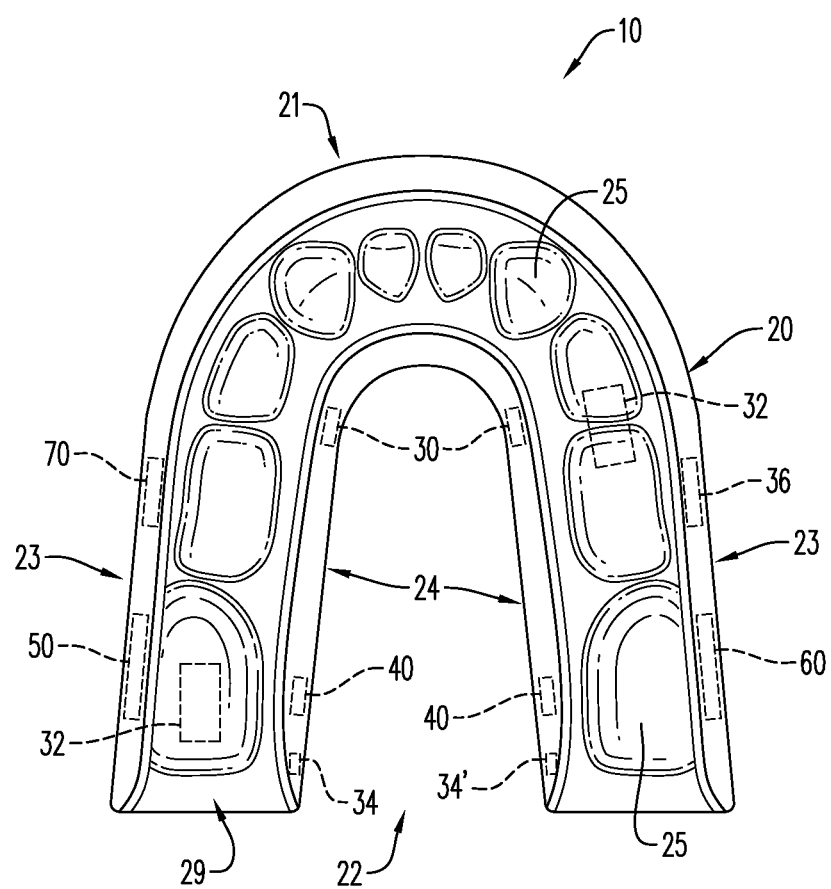
FIG. 2 is a top view of an oral appliance, according to an embodiment.
Figure 3:
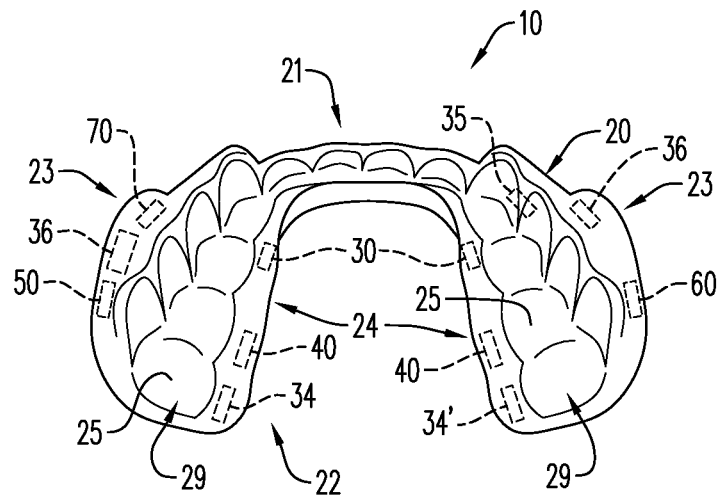
FIG. 3 is a perspective view of an oral appliance, according to an embodiment.
Figure 4:
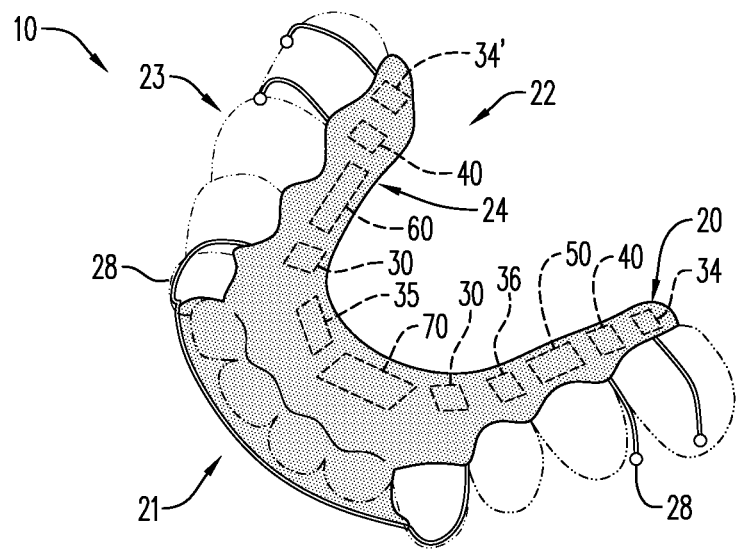
FIG. 4 is a perspective view of an oral appliance, according to an embodiment.

In an embodiment, and with particular reference to FIGS. 2-4, an oral appliance 10 for treatment of sleep apnea in a user is provided. The oral appliance 10 is illustrated as having a mouthpiece 20 and several components. In an embodiment, the mouthpiece 20 is "customizable", that is, customized to the individual user's mouth in such a manner that it provides for a comfortable fit over and around surfaces of the user's hard (teeth/dentition) and/or soft tissues (general mouth structure, including gums). When customized, the mouthpiece 20 may fit over temporary, permanent, primary natural and/or artificial lower dentition of adult and/or child users. The mouthpiece 20 may be configured to receive a removable denture of the user. According to an aspect, the mouthpiece 20 is fabricated over the lower jaw, that is, the mandible, with partial or complete absence of dentition. When customized, the mouthpiece 20 can be formed of any self-conforming material that may be adaptable to variances and/or changes in mouth structure, or through use of a dental impression of the individual user's dentition, as would be understood by a person having ordinary skill in the art. In other words, a mandibular impression and/or a dental impression can be taken, whereby a negative imprint of the user's hard and/or soft tissues are used to create a positive reproduction (or cast) customized for the user.

The types of materials selected to form the mouthpiece 20 would be known to one of ordinary skill in the art and includes polymers, thermoplastics, acrylics, silicone, rubber, metal wires or any other material that can be used to form the mouthpiece 20 conformed to the user's dentition. In an embodiment, the materials are medical-grade, latex-free, BPA-free and any other material known to minimize patient health risks. According to an aspect, the mouthpiece 20 may be formed from the impression made in a thin, resilient material.

In an embodiment and as illustrated in FIGS. 2 and 3, the mouthpiece 20 includes a central channel 29 bounded by a lingual portion 24 and a buccal portion 23. The central channel 29 may be configured to be receivably positioned over and/or receive one or more of the user's dentition such that the mouthpiece 20 is secured thereon. When the mouthpiece 20 is in use, the central channel 29 may receive the user's dentition and may extend over and/or cover occlusal or bite surfaces of the user's teeth. The lingual portion 24 of the mouthpiece 20 extends between the user's teeth and the user's tongue. In an embodiment and as illustrated in FIGS. 2 and 3, the buccal portion 23 of the mouthpiece 20 extends between the user's teeth and the user's cheek.

According to an aspect, the mouthpiece 20 is configured to be secured to the user's dentition. In an embodiment and as illustrated in FIG. 4, the mouthpiece 20 includes the lingual portion 24 and dentition attachment members 28 coupled to the lingual portion 24. The dentition attachment members 28, as well as the lingual portion 24, may be customizable, such that the dentition attachment members 28 have a shape and size that substantially conforms to the dentition of the user, thereby providing the user with the mouthpiece 20 having a secured and customized fit. Typically, the dentition attachment members 28 are provided in a wire-frame form, in a way that extends from the lingual portion 24 to wrap over or around the individual user's dentition and anchor the lingual portion 24 between the lingual surface of the teeth and the tongue. According to an aspect, at least a portion of the dentition attachment members 28 is shaped to form a retention loop around one or more teeth of the user.

Similar to the dentition receiving cavities 25 described for the mouthpiece 20 of FIGS. 2 and 3, the lingual portion 24 depicted in FIG. 4 may also be customized to have a shape that is substantially the same as the shape of the individual user's dentition for which it has been molded and/or shaped to fit, thereby assisting the retention function of the dentition attachment members 28. In any event, the mouthpiece 20 is capable of being at least temporarily fixed in place by virtue of having been molded and conformed to the dentition of the user and/or being provided with the dentition attachment members 28, thus providing the customized fit. As such, the mouthpiece 20 may provide a retention function thereby allowing the oral appliance 10 to remain in place during the user's sleep, particularly in situations where the user may make slight to moderate movements during sleep and/or when the user may be awake. Thus, the mouthpiece 20 may be substantially immovable unless positive effort is applied to remove the mouthpiece 20. In other words, the user may remove the mouthpiece 20 at any time, if desired, by exerting a little pressure to remove the mouthpiece 20. Since the mouthpiece 20 is not permanently affixed to the dentition, it can be worn and/or subsequently removed by the user at any time. Therefore, the oral appliance 10 may be used for varying lengths of time.

According to an aspect and as illustrated in FIGS. 2-4, the components positioned on and/or embedded within the mouthpiece 20 include one or more of the following components: an oxygen sensor 30, a pressure sensor 32, an airflow sensor 34, a noise detector 35, an actigraphy sensor 36, a stimulator 40, a microprocessor 50, a data recorder 60 and a battery 70. According to an aspect, the mouthpiece 20 includes dry protective areas or covering to these electronic components that substantially inhibit and/or limit water and/or tissue damage to the components (not shown). Such dry/protected zones may be formed by virtue of the components being embedded within the mouthpiece 20 itself.

As illustrated in FIGS. 2-4, the oxygen sensor(s) 30 may be provided near an anterior portion 21 of the mouthpiece 20, i.e., towards the user's lips and away from the user's pharynx. According to an aspect, the oxygen sensor 30 is configured to monitor and/or determine actual oxygen saturation levels of the user's hemoglobin. The oxygen sensor 30 may be adapted to monitor and/determine the pulse and/or heart rate of the user. The oxygen sensor 30 may be positioned on or in the lingual portion 24 of the mouthpiece 20. In an embodiment, the oxygen sensor 30 is positioned primarily towards lateral portions of the tongue, which are generally understood to be the most vascular areas of the tongue, i.e., having numerous blood vessels. According to an aspect, the oxygen sensor 30 is a transceiver such as a pulse oximeter configured to monitor/sense the oxygen saturation level of a user by analyzing the change in color of the user's blood. The pulse oximeter may measure the pulse rate of the user, typically in beats per minute, based on variations and/or deviations in the user's oxygen saturation level. An exemplary pulse oximeter, for example, may include light emitting diodes configured to transmit red and infrared lights to vascular surfaces of the user's tongue and sense changes in oxygen level in the user's tongue. According to an aspect, two oxygen sensors 30 are provided on the lingual portion 24 of the mouthpiece 20. The two oxygen sensors 30 may be bilaterally positioned on the mouthpiece 20. While FIGS. 2-4 illustrate two oxygen sensors 30 being positioned on the mouthpiece 20, it is to be understood that the number of oxygen sensors provided may be 3, 4, 5, 6 or more.

According to an aspect and as illustrated in FIGS. 2 and 3, the oral appliance 10 may include one or more pressure sensors 32. According to an aspect, the one or more pressure sensors 32 are configured to detect signs of clenching and/or grinding by the user that occur, for example, while the user is asleep. The pressure sensors 32 may be positioned in or on the central channel 29. In an embodiment, the pressure sensors 32 are positioned in the dentition receiving cavities 25, such that the pressure sensors 32 are positioned substantially adjacent to the user's mandibular occlusal and/or bite surfaces. According to an aspect, the pressure sensors 32 are on an exterior surface of the central channel 29, where the central channel 29 has an interior surface configured for receiving the dentition receiving cavities 25 and the exterior surface is positioned opposite of the interior surface, such that the pressure sensors 32 are positioned substantially adjacent to the user's maxillary occlusal and/or bite surfaces. In some embodiments (not shown), the pressure sensors may be provided on the dentition attachment members 28, such as those manufactured by Tekscan under the brand Flexi-Force™ Force Sensors. Such signs of clenching may include force sensors configured to measure the force that is being applied to occlusal and/or bite surfaces of the user's teeth. According to an aspect, the pressure sensors 32 are a thin resilient material. The one or more pressure sensors 32 may be electrically sealed and/or impervious to liquids, saliva and/or oral tissue. The number of pressure sensors 32 provided on the mouthpiece 20 may be selected based on the user's proclivity to grinding and/or clenching. According to an aspect, the number of pressure sensors 32 provided is 2, 3, 4, 5, 6 or more.

In an embodiment, the mouthpiece 20 includes one or more airflow sensors 34 configured to measure the actual airflow and/or breathing rate of the user, i.e., the rate of air that is inhaled and/or exhaled through the mouthpiece 20 by the user. According to an aspect, the airflow sensor 34 is configured to detect any reduction and/or cessation of airflow during sleep. The airflow sensor 34 may be arranged at any position on the mouthpiece 20 that is in a general flow path of air inhaled and/or exhaled by the user. As illustrated in FIG. 2, the airflow sensor 34 may be positioned near a posterior portion 22 of the mouthpiece 20. According to an aspect, the airflow sensor 34 is bilaterally positioned on the mouthpiece 20. As illustrated in FIGS. 2-3, one airflow sensor 34 may be positioned to the left of the lingual portion 24, while another airflow sensor 34' may be positioned to the right of the lingual portion 24. In any event, both airflow sensors 34, 34' may work in tandem to measure the user's airflow rate. Airflow sensors 34 may be arranged in/on at least one of the lingual portion 24 and the buccal portion 23 of the mouthpiece 20. The number of airflow sensors 34 provided on the mouthpiece may be selected based on the needs of the user. According to an aspect, the number of airflow sensors provided is 2, 3, 4, 5 or more.

According to an aspect and as illustrated in FIGS. 2-4, the mouthpiece 20 may include an actigraphy sensor 36 configured to monitor and capture data related to sleep activity, including sleep position and movement of the user during sleep. The actigraphy sensor 36 may embedded in or otherwise connected to the mouthpiece 20, at any desired position. According to an aspect and as illustrated in FIG. 2-3, the actigraphy sensor 36 is position at the buccal portion 23 of the mouthpiece 20. In an alternate embodiment and as illustrated in FIG. 4, the actigraphy sensor 36 may be positioned at the lingual portion 24 of the mouthpiece 20. The actigraphy sensor 36 may determine the user's sleep positions, such as, for example, a supine position during which the user is positioned on his/her back, a prone position during which the user is lying face down and/or lateral recumbent positions during which the user is lying on their left or right sides. The actigraphy sensor 36 may measure the time the user sleeps in each identified position and/or the frequency of the user changing from one sleep position to another sleep position.

The oral appliance 10 may include a noise detector 35 configured to detect actual noise and/or vibrations caused by the user's snoring. According to an aspect, the noise detector 40 is internally hard-wired to one or more components coupled to or otherwise embedded in the mouthpiece 20, such as, for example, the stimulator 40, the microprocessor 50 and the data recorder 60, such that the noise detector 40 can communicate with the components. The noise detector 35 may be configured to wirelessly communicate with at least one of the stimulator 40, the microprocessor 50 and the data recorder 60. The noise detector 35 may be positioned on or otherwise embedded in the mouthpiece 20 at any desired location. According to an aspect, the noise detector 35 is positioned at the posterior portion 22 of the mouthpiece 20, such that relevant snoring information may be detected close to a sound source, i.e., the user's pharynx. In an embodiment, the noise detector 34 is positioned at the anterior portion 21 of the mouthpiece 20. As illustrated in FIG. 3, the noise sensor 35 may be positioned at the buccal portion 23 of the mouthpiece 20. In an embodiment and as illustrated in FIG. 4, the noise sensor 35 is positioned at the lingual portion 24 of the mouthpiece 20. While FIGS. 3-4 illustrate a single noise detector 35 being provided on the mouthpiece 20, it is to be understood that 2, 3, 4 or more noise detectors 35 may be provided.

According to an aspect and as illustrated in FIGS. 2-4, the at least one stimulator 40 is provided near the posterior portion 22 of the mouthpiece 20, that is generally near the back of the user's mouth. The stimulator 40 is configured to provide a gentle stimulation to the tongue of the user, as will be described in more detail hereinbelow. In an embodiment, the stimulator 40 is positioned on the lingual portion 24 of the mouthpiece 20, adjacent to the tongue. The stimulator 40 may be bilaterally positioned on the mouthpiece 20, such that bilateral stimulation may be provided to both sides of the user's tongue. The stimulator 40 may be positioned substantially adjacent to a base of the user's tongue, for example, adjacent to the user's genioglossus muscle. Thus, the stimulator 40 may be configured for providing stimulation to the genioglossus muscle of the user's tongue in a manner that allows the muscle tone of the genioglossus muscle to be regained. Such stimulation may be electrical impulses that cause the genioglossus muscle to contract and/or cause the user to reduce the amount of force being applied to occlusal and/or bite surfaces of the user's teeth. In some embodiments, contraction of the genioglossus muscle may cause the user's tongue to protrude, thereby creating more space in the user's pharynx and helping the user breathe more easily in a manner that increases the oxygen saturation levels of the user's hemoglobin. The stimulation may be in response to the actual saturation level of hemoglobin of the user, as measured by the at least one oxygen sensor 30.

According to an aspect, the stimulator 40 is activated based on measurements received from the oxygen sensors 30, the pressure sensors 32, the airflow sensors 34 and/or the noise detector 35. The stimulator 40 may be activated if the oxygen sensor 30 determines that the actual oxygen saturation level of hemoglobin of the user is at a predetermined oxygen level, that is, that a certain oxygen level has been pre-determined to be insufficient. The stimulator 40 may provide at least intermittent stimulation to the genioglossus muscle of the user's tongue until the oxygen saturation level of hemoglobin rises above the predetermined oxygen level.

In an embodiment, the stimulator 40 is activated if the oxygen sensor 30 determines that the actual oxygen saturation level of hemoglobin of the user is below about 95% oxygen saturation. Stimulation of the user's genioglossus muscle may facilitate an increase in respiratory flow to the user, thereby increasing the availability of oxygen to the user and the increase of oxygen saturation levels of hemoglobin. According to an aspect, when the oxygen sensor 30 determines that the oxygen saturation level of hemoglobin of the user is above about 95% oxygen saturation, the stimulator 40 is not activated. In an embodiment, the stimulator 40 is activated if the pressure sensors 32 detect grinding and/or clenching by the user. According to an aspect, the stimulator 40 provides stimulation until the force applied to occlusal and/or bite surfaces of the user's teeth are below a predetermined force level. The stimulator 40 may stop stimulation once the pressure sensors 32 detect that grinding and/or clenching has substantially decreased and/or ceased, as evidenced by the detected force level. According to an aspect, the stimulator 40 is activated when the airflow sensor 34 determines that the frequency of air inhaled and/or exhaled by the user is below a predetermined airflow level. In an embodiment, the stimulator 40 is activated when the airflow sensor 34 determines that airflow is at or below 30% of the user's natural airflow or breathing rate, i.e., air inhaled and/or air exhaled by the user while the user is awake (natural airflow), has been reduced by 30%. The stimulator 40 may provide stimulation to the genioglossus muscle until the predetermined airflow level is achieved and/or airflow to the user is at least about 30% of the user's natural airflow rate. In an embodiment, the stimulator 40 is activated if the noise detector 35 detects that the actual noise and/or vibrations are above a predetermined noise level. In this embodiment, the stimulator 40 provides gentle electrical stimulation to the genioglossus muscle of the user's tongue until the actual noise and/or vibrations are below the predetermined noise level.

In an embodiment, the stimulator 40 is configured to provide constant stimulation to the genioglossus muscle of the user's tongue. Alternatively, the stimulator 40 may provide variant stimulation to the genioglossus muscle of the user's tongue. The variant stimulation may increasingly stimulate the genioglossus muscle of the tongue until the oxygen saturation level is at the predetermined oxygen level, such as, for example, at or above 95%. In an embodiment, the variant stimulation increasingly stimulates the genioglossus muscle until the force applied to the occlusal and/or bite surfaces is below the predetermined force level. The variant stimulation provided by the stimulator 40 to may increasingly stimulate the genioglossus muscle until the predetermined airflow level is achieved and/or until the actual noise and/or vibrations are below the predetermined noise level. According to an aspect, the strength and frequency of the electrical impulses in variant mode will depend on how quickly the oxygen saturation of hemoglobin and/or the predetermined force level is achieved. The constant or variant stimulation may be a gentle stimulation that does not disturb and/or awaken the user during sleep. According to an aspect, the constant or variant stimulation is gentle enough so that the user does not recognize it when wearing it when the user is at least slightly awake. The stimulator 40 may alternate between a constant stimulation mode and a variant stimulation mode. In an embodiment, the at least one stimulator 40 is an electrode configured to provide gentle electrical impulses. The gentle electrical impulses may be provided to the genioglossus muscle of the user's tongue in a non-invasive manner and in such a manner that stimulation does not awaken the user during sleep.

As illustrated in FIGS. 2-4, a microprocessor 50 may be provided on and/or embedded within the mouthpiece 20. As illustrated in FIGS. 2 and 3, the microprocessor 50 may be positioned on or in the buccal portion 23. Alternatively, and as illustrated in FIG. 4, the microprocessor 50 may be positioned on or in the lingual portion 24 of the mouthpiece 20. In other words, it is possible to place the microprocessor 50 on the mouthpiece 20 wherever available real estate may be found. Thus, when more than one component, such as, for example, the oxygen sensor 30 and the stimulator 40, are positioned at the lingual portion 24 of the mouthpiece 20, the microprocessor 50 may be positioned away from these regions on the buccal portion 23. In some embodiments and as illustrated in FIG. 4, the microprocessor 50 is positioned at the lingual portion 24 of the mouthpiece 20 and may be embedded therein. It is to be understood that the microprocessor 50 may be positioned at any location that enables it to communicate with the components included in the oral appliance 10, such as, for example, the oxygen sensor 30, the pressure sensor 32, the airflow sensor 34, the noise detector 35, the actigraphy sensor 36, the stimulator 40, the data recorder 60, and/or a battery 70, while ensuring that the location of the microprocessor 50 helps maintain a comfortable fit and/or maintain wearability of the mouthpiece 20 by the user. The microprocessor 50 may be attached to and/or positioned at any desired location on the mouthpiece 20, such as, anteriorly, posteriorly and any location therebetween. According to an aspect, the microprocessor 50 is sized and/or positioned to provide for a comfortable fit for the user. To be sure, the microprocessor 50 may be positioned at any location that does not interfere with the comfortable fit of the mouthpiece 20 for the user. The microprocessor 50 may be configured to receive data corresponding to the actual oxygen saturation levels of hemoglobin from the at least one oxygen sensor 30, and data relating to the user's grinding and/or clenching behavior, actual airflow levels, actual noise and/or snoring levels. In an embodiment, the microprocessor 50 is configured to activate the stimulator 40 if the oxygen sensor 30 determines that the actual oxygen saturation level of hemoglobin of the user is at a predetermined level. According to an aspect, the microprocessor 50 activates the stimulator 40 if the pressure sensor 32 determines that the user is clenching and/or grinding his/her dentition at unacceptable levels. The microprocessor 50 may activate the stimulator 40 if the airflow sensor 34 determines that the user's airflow rate is below the predetermined airflow level. According to an aspect, the microprocessor 50 activates the stimulator if the noise detector 35 determines that the user's actual noise and/or vibrations during sleep are above the predetermined noise level.

As illustrated in FIGS. 2-4 and in an embodiment, the oral appliance 10 includes a data recorder 60. The data recorder 60 may be positioned at, for instance, the buccal portion 23 of the mouthpiece 20, (see, for instance, FIG. 2). According to an aspect and as illustrated in FIG. 3, the data recorder 60 is positioned at the lingual portion 24 of the mouthpiece 20. In an embodiment, the data recorder 60 is configured to receive and/or store information provided from the microprocessor 50. According to an aspect, the data recorder 60 receives and/or stores the actual oxygen saturation level of hemoglobin, the predetermined force level of the user applied to the occlusal and/or bite surfaces and/or the predetermined airflow level, as provided by the oxygen sensor 30, the pressure sensors 32 and the airflow sensor 34, respectively. The data recorder 60 may also receive and/or store stimulation information regarding the quantity and/or frequency of stimulations provided by the stimulator 40.

According to an aspect, the appliance 10 includes a transceiver (not shown). The transceiver may be configured to remotely monitor any additional components provided on and/or within the mouthpiece 20. In an embodiment, the transceiver may be configured for use with a customized web-based application for a handheld wireless communication device. The customized web-based application may include features such as, a graph of the user's sleep position and chart and/or graphical data related to oxygen saturation levels of hemoglobin and the pressure applied to occlusal surfaces of the user's dentition. According to an aspect, the customized web-based application may include data related to the user's heart rate. In an embodiment, the transceiver communicates with handheld wireless communication devices having Bluetooth® capabilities. The transceiver may be communicable with handheld wireless communication devices, such as, for example, computers, smart watches, smart phones, and the like.

The oral appliance 10 may include a battery 70. While it is contemplated that the battery 70 is rechargeable, it may be disposable. The battery 70 may be configured to provide power to at least one of the oxygen sensor 30, the pressure sensor 32, the airflow sensor 34, the noise detector 35, the actigraphy sensor 36, the stimulator 40, the microprocessor 50, the data recorder 60 and the transceiver. According to an aspect, the battery 70 includes an energy store and a contact element sealably arranged on the mouthpiece 20 (not shown). In an embodiment, the battery 70 is embedded within the mouthpiece 20, such that the battery 70 is not exposed to liquids, saliva and/or oral tissue. The battery 70 may be positioned near the buccal portion 23 (see, for instance, FIG. 2). According to an aspect, the battery 70 is positioned near the lingual portion 24 (see, for instance FIG. 4) of the mouthpiece 20.

Figure 5:
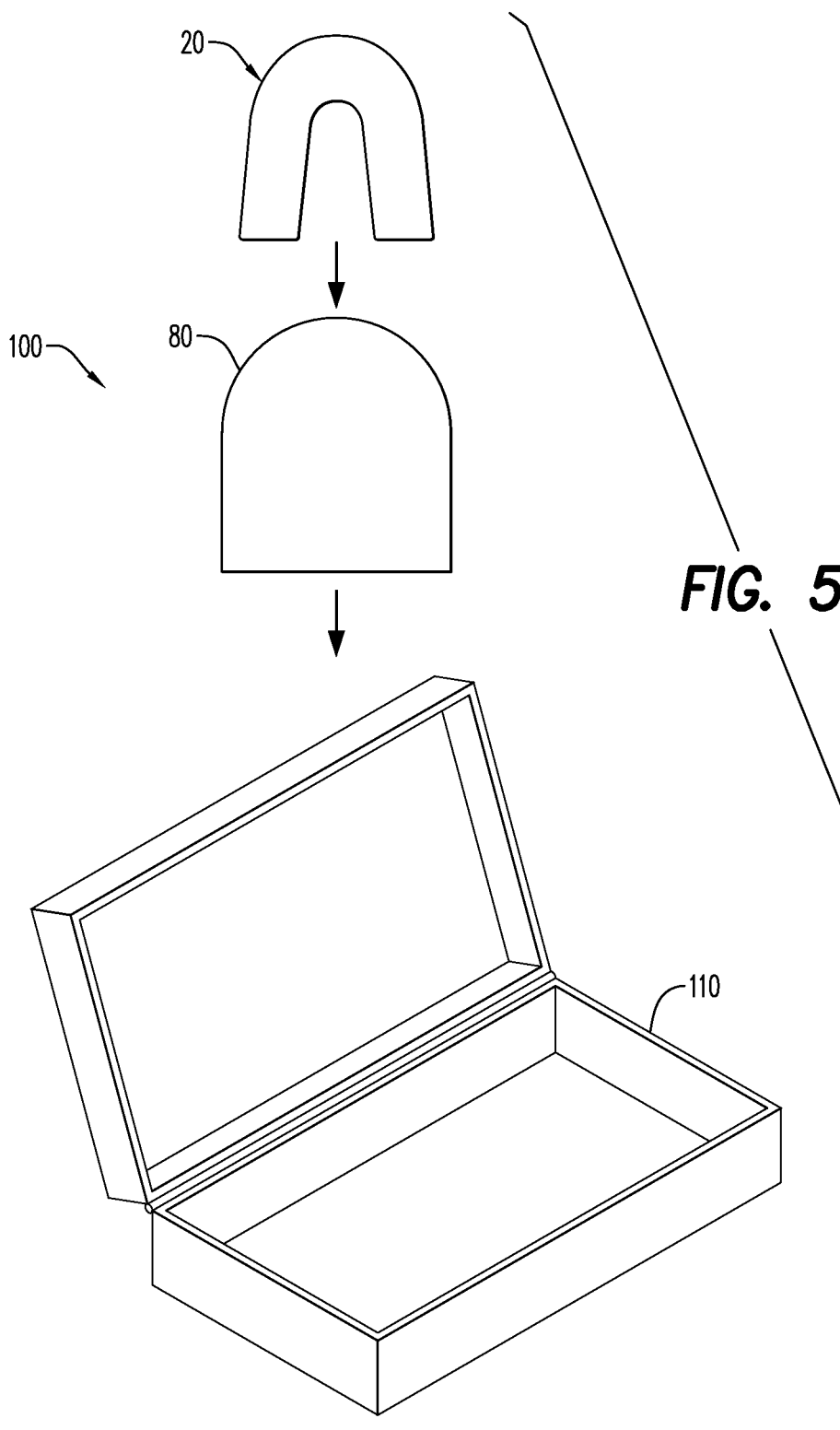
FIG. 5 is a perspective view of an oral appliance kit, according to an embodiment.

As illustrated in FIG. 5, the oral appliance may include a data transfer pod 80. The data transfer pod 80 may be configured to charge and/or provide power to the rechargeable battery 70. According to an aspect the data transfer pod 80 is configured to retrieve and/or store information collection by the data recorder 60, such that the user and or medical provider can track and/or assess the collected information. According to an aspect, the transceiver may include power amplifiers (not shown) configured to reduce power requirements of the oral appliance 10, thereby helping to conserve life of the rechargeable battery 70. The data transfer pod 80 may be provided with an electrical contact component accessible to a plug of a power supply unit (not shown).

As illustrate in FIG. 5 and in an embodiment, an oral appliance kit 100 for treatment of sleep apnea in a user is provided. In an embodiment, the oral appliance kit 100 includes the oral appliance 10, including the various electronic components, as substantially described above and illustrated in FIGS. 2-4, and the data transfer pod 80.

FIG. 6 is a flowchart illustrating an exemplary operation 200 of the oral appliance 10. Optionally, a customized mouthpiece is created 201 and various electronic components are assembled to form the oral appliance. The mouthpiece of the oral appliance is positioned 210 in the user's oral cavity. Oxygen sensors measure 220 oxygen saturation levels of the users hemoglobin, pressure sensors measure 222 the pressure applied to occlusal surfaces of the customized mandibular mouthpiece, airflow sensors measure 224 the actual airflow and/or breathing rate of the user, actigraphy sensors measure 226 data related to sleep activity, including sleep position and movement of the user during sleep and/or noise detectors measure 228 the actual noise and/or vibrations created by the user during sleep. The microprocessor collects, records and analyzes data 230 relating to oxygen saturation, pressure, airflow, sleep activity and actual noise levels. In the event that actual oxygen saturation levels of hemoglobin are below a predetermined level or in the event that the actual pressure applied to the occlusal portion of the mouthpiece is above the predetermined pressure level, the stimulator sends impulses 240 to stimulate the genioglossus muscle of the user's tongue. The oxygen sensors re-measure 250 the oxygen saturation level of hemoglobin, the pressure sensor re-measures 252 the pressure applied to occlusal surfaces of the customized mandibular mouthpiece, the airflow sensors re-measure 254 actual airflow of the user, the actigraphy sensors re-measure 256 the user's sleep activity, and the noise detector re-measures 258 the actual noise and/or vibrations created by the user during sleep. Stimulation is stopped if the predetermined levels are achieved. If the predetermined levels are not achieved, stimulation continues, increases, decreases or otherwise varies according to the measured values.

The components of the apparatus illustrated are not limited to the specific embodiments described herein, but rather, features illustrated or described as part of one embodiment can be used on or in conjunction with other embodiments to yield yet a further embodiment. It is intended that the apparatus include such modifications and variations. Further, steps described in the method may be utilized independently and separately from other steps described herein.

While the apparatus and method have been described with reference to specific embodiments, it will be understood by those skilled in the art that various changes may be made and equivalents may be substituted for elements thereof without departing from the scope contemplated. In addition, many modifications may be made to adapt a particular situation or material to the teachings found herein without departing from the essential scope thereof.

In this specification and the claims that follow, reference will be made to a number of terms that have the following meanings. The singular forms "a," "an" and "the" include plural referents unless the context clearly dictates otherwise. Furthermore, references to "one embodiment", "some embodiments", "an embodiment" and the like are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Terms such as "first," "second," "upper," "lower" etc. are used to identify one element from another, and unless otherwise specified are not meant to refer to a particular order or number of elements.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited thereto, "consisting essentially of" and "consisting of." Where necessary, ranges have been supplied, and those ranges are inclusive of all sub-ranges therebetween. It is to be expected that variations in these ranges will suggest themselves to a practitioner having ordinary skill in the art and, where not already dedicated to the public, the appended claims should cover those variations.

Advances in science and technology may make equivalents and substitutions possible that are not now contemplated by reason of the imprecision of language; these variations should be covered by the appended claims. This written description uses examples to disclose the method, machine and computer-readable medium, including the best mode, and also to enable any person of ordinary skill in the art to practice these, including making and using any devices or systems and performing any incorporated methods. The patentable scope thereof is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal language of the claims.

What is claimed is:

1. An oral appliance for treatment of sleep apnea in a user, comprising:
    a mouthpiece for being received in an oral cavity of the user;
    at least one pulse oximeter attached to the mouthpiece, wherein the pulse oximeter is configured to monitor actual oxygen saturation levels of hemoglobin of the user; and
    at least one stimulator attached to the mouthpiece and configured for providing stimulation to the user in response to the actual oxygen saturation level of hemoglobin of the user.

2. The oral appliance of claim 1, wherein the stimulator provides constant stimulation or variant stimulation to a genioglossus muscle of the user's tongue until the oxygen saturation level of hemoglobin rises above the predetermined level.

3. The oral appliance of claim 1, wherein the stimulator is activated if the at least one pulse oximeter determines that the actual oxygen saturation level of hemoglobin of the user is below about 95% oxygen saturation.

4. The oral appliance of claim 1, further comprising one or more pressures sensors positioned at an occlusal portion of the mouthpiece and configured for measuring actual pressure applied to the mouthpiece.

5. The oral appliance of claim 1, further comprising a noise detector attached to the mouthpiece, wherein the noise detector is configured to detect actual noise and/or vibrations caused by snoring of the user.

6. The oral appliance of claim 1, further comprising one or more airflow sensors configured for measuring actual airflow of the user, wherein the stimulator is activated only if the actual airflow is below a predetermined airflow level, and
    the stimulator provides electrical stimulation to a genioglossus muscle of the user's tongue until the actual airflow level is at or above the predetermined airflow level.

7. The oral appliance of claim 1, further comprising:
    an actigraphy sensor attached to the mouthpiece, wherein the actigraphy sensor is configured to monitor and capture at least one of the user's sleep position and the user's movement during sleep.

8. The oral appliance of claim 1, further comprising:
    a microprocessor configured to receive data corresponding to the actual oxygen saturation level of hemoglobin from the at least one pulse oximeter and to activate the at least one stimulator.

9. The oral appliance of claim 8, further comprising:
    a rechargeable battery secured to the mouthpiece and configured for providing power to one or more sensors, the at least one stimulator, the microprocessor and the pulse oximeter.

10. An oral appliance for treatment of sleep apnea in a user, comprising:
    a mouthpiece for being received in an oral cavity of the user;
    at least one pulse oximeter attached to the mouthpiece, wherein the pulse oximeter is configured to monitor actual oxygen saturation levels of hemoglobin of the user;
    at least one stimulator attached to the mouthpiece, wherein the stimulator is configured for providing stimulation to a genioglossus muscle of a tongue of the user when the actual oxygen saturation level is below about 95% oxygen saturation; and
    a microprocessor attached to the mouthpiece, the microprocessor being configured to receive data corresponding to the actual oxygen saturation level of hemoglobin and to activate the at least one stimulator.

11. The oral appliance of claim 10, further comprising at least one of:
    one or more pressures sensors positioned at an occlusal portion of the mouthpiece and configured for determining actual pressure applied to the mouthpiece;
    a noise detector attached to the mouthpiece, wherein the noise detector is configured to detect actual noise and vibrations caused by snoring of the user; and
    an actigraphy sensor attached to the mouthpiece, the actigraphy sensor being configured to monitor and capture at least one of the user sleep position and the user's movement during sleep.

12. The oral appliance of claim 11, further comprising:
    a rechargeable battery attached to the mouthpiece, the rechargeable battery being configured for providing power to at least one of the at least one pulse oximeter, the one or more pressure sensors, the actigraphy sensor, the noise detector, the at least one stimulator and the microprocessor.

13. The oral appliance of claim 11, wherein the stimulator is activated by at least one of the following events:
    an airflow sensor determines that the user's airflow rate is below a predetermined airflow level;
    the pressure sensors determine that the actual pressure applied to the mouthpiece by the user clenching or grinding dentition is at unacceptable levels; and
    the noise detector determines that actual noise and vibrations caused by snoring of the user are above a predetermined noise level.

14. The oral appliance of claim 11, wherein the microprocessor is further configured to receive and store data related to at least one of the actual pressure applied to the mouthpiece, the actual noise and vibrations caused by snoring of the user, and the user's sleep position and movement during sleep.

15. The oral appliance of claim 14, further comprising:
a data recorder attached to the mouthpiece, the data recorder being configured to receive and store information provided from the microprocessor.

16. An oral appliance kit for treatment of sleep apnea in a user, comprising:
an oral appliance, the oral appliance comprising:
a mouthpiece for being received in an oral cavity of the user;
at least one pulse oximeter attached to the mouthpiece, the pulse oximeter being configured to monitor actual oxygen saturation levels of hemoglobin of the user;
at least one stimulator attached to a posterior portion of the mouthpiece, wherein the stimulator provides stimulation to a genioglossus muscle of a tongue of the user;
a microprocessor attached to the mouthpiece, the microprocessor being configured to receive data corresponding to the actual oxygen saturation level of hemoglobin and to activate the at least one stimulator; and
a data recorder attached to the mouthpiece, the data recorder being configured to receive and store information provided from the microprocessor.

17. The oral appliance kit of claim 16, further comprising:
a rechargeable battery attached to the mouthpiece and configured to provide power to the at least one pulse oximeter, the at least one stimulator, the microprocessor and the data recorder; and
a data transfer pod configured to charge the rechargeable battery and retrieve and store information collected by the data recorder.

18. The oral appliance kit of claim 17, wherein the data transfer pod is configured to store and transport the oral appliance.

19. The oral appliance kit of claim 16, further comprising at least one of:
one or more pressures sensors positioned at an occlusal portion of the mouthpiece and configured for determining actual pressure applied to the mouthpiece;
a noise detector attached to the mouthpiece, wherein the noise detector is configured to detect actual noise and vibrations caused by snoring of the user; and
an actigraphy sensor attached to the mouthpiece, the actigraphy sensor being configured to monitor and capture at least one of the user sleep position and the user's movement during sleep.

20. The oral appliance kit of claim 19, wherein the stimulator is activated by at least one of the following events:
an airflow sensor determines that the user's airflow rate is below a predetermined airflow level;
the pressure sensors determine that the actual pressure applied to the mouthpiece by the user clenching or grinding dentition is at unacceptable levels; and
the noise detector determines that actual noise and vibrations caused by snoring of the user are above a predetermined noise level.

\* \* \* \* \*